(12) United States Patent
Dickopf et al.

(10) Patent No.: US 6,441,906 B2
(45) Date of Patent: Aug. 27, 2002

(54) SET-UP OF MEASURING INSTRUMENTS FOR THE PARALLEL READOUT OF SPR SENSORS

(75) Inventors: Stefan Dickopf; Kristina Schmidt; Dirk Vetter, all of Heidelberg (DE)

(73) Assignee: Graffinity Pharmaceutical Design GmbH, Heidelberg (DE)

( * ) Notice: Subject to any disclaimer, the term of this patent is extended or adjusted under 35 U.S.C. 154(b) by 0 days.

(21) Appl. No.: 09/859,677

(22) Filed: May 18, 2001

Related U.S. Application Data (63) Continuation of application No. PCT/EC99/08977, filed on Nov. 16, 1999.

(51) Int. Cl.[7] ............................................. G01N 21/55
(52) U.S. Cl. ........................................................ 356/445
(58) Field of Search .......................................... 356/445

(56) References Cited

U.S. PATENT DOCUMENTS

| | | | | |
|---|---|---|---|---|
| 4,931,384 A | * | 6/1990 | Layton et al. | 356/317 |
| 5,485,277 A | * | 1/1996 | Foster | 356/445 |
| 5,779,978 A | | 7/1998 | Hartmann et al. | |

FOREIGN PATENT DOCUMENTS

| | | |
|---|---|---|
| DE | 196 15 366 | 10/1997 |
| WO | 95/22754 | 8/1995 |

OTHER PUBLICATIONS

Zizlsperger, M., et al., "Multispot parallel on–line monitoring of interfacial binding reactions by surface plasmon microscopy". Progress in Colliod & Polymer Science, 109:244–253 (1998).

\* cited by examiner

Primary Examiner—Richard A. Rosenberger
(74) Attorney, Agent, or Firm—Nath & Associates PLLC; Gary M. Nath; Marvin C. Berkowitz (57) ABSTRACT

The invention relates to a set-up of measuring instruments for the parallel readout of SPR sensors. The aim of the invention is to provide a measuring arrangement for the parallel readout of a plurality of SPR sensors, wherein the readout process should be terminated within an integration period of less than 30 minutes. To this end, a wavelength-selective component (5) and an optical imaging system (L2, L3) are arranged downstream of a light source (3). Said optical imaging system (L2, L3) is in such a manner that at a first wavelength it guarantees a parallel illumination of the light entrance sides of the waveguides (13) which are provided with SPR-compatible sensor zones, and that the light emerging from the individual light waveguides (13) may simultaneously be imaged onto a CCD chip (20) via an optical system (L4) in such a way that the light emerging from each individual light waveguide (13) is respectively detectable by several adjacent CCD pixels of the CCD chip (20), and from these pixel areas a respective light intensity value is calculable by means of image processing software, and, after data storage of an intensity value, a set wave length and coordinate in the waveguide array (10), an adjustment of the wavelength-selective assembly (5) to a second, arbitrarily providable, further light wavelength is performable by means of a computer (30) via a control line (31).

24 Claims, 9 Drawing Sheets

SET-UP OF MEASURING INSTRUMENTS FOR THE PARALLEL READOUT OF SPR SENSORS

This is a Continuation Application of PCT Application No. PCT/EC99/08977, filed Nov. 16, 1999.

DESCRIPTION

The invention relates to a measurement assembly for parallel readout of surface plasmon resonance (SPR) sensors.

In the search for new active substances combinatorial chemical systems hold high promise in finding ligands matching a receptor molecule. Miniaturizing and automating synthesis and parallelization thereof is salient to assaying as large a number of ligands as possible. Due to the small resulting amounts of ligand, these requirements (miniaturizing, automating and parallelizing) apply likewise to detecting the ligand receptor binding for which the high sensitivity of the SPR method can be used in which the light reflected from a thin gold film is detected. Under a suitable resonance condition (angle of incidence and wavelength of the light and thickness of the gold film) the intensity of the reflected light is reduced. The energy of the light is then transformed into charge density waves of the electron gas in the gold film, these charge density waves being termed plasmons.

There are two methodical approaches to observing the resonance: either monochromatic light is used in plotting the intensity of the reflected light as a function of the angle of incidence or the angle of incidence is maintained constant and the wavelength of the light is varied. In both cases the resonance curve is shifted with a change in the refractive index of the medium provided on the side of the gold film facing away from incident light.

This effect is made use of in biochemical analysis. The receptor or ligand is immobilized on the gold surface. After addition of the ligand or receptor the resonance condition is changed on molecular association.

The simplest assembly for measuring this effect is a glass prism which is illuminated with light and the angle of incidence of which is varied (see e.g. "Biospecific interaction analysis using biosensor technology" Malmqvist, M., Nature 361 (1993) 186–187).

A more sophisticated method is the parallel detection of multiple angles in which the gold surface is illuminated with a slightly divergent beam of monochromatic light (aperture angle ~10°) and the reflected light is directed to a position resolving light detector for obtaining an explicit assignment between the angle of reflection and the position on the detector. This construction has the advantage of sensing the angle range of interest with no moving parts. This is why use is made of this kind of detection in a few commercial systems as disclosed e.g. in WO 90/05295 A1 or EP 797 091 A1. One disadvantage of these assemblies is that only one prepared array of gold sensors (one-dimensional detection) or but a few arrays of sensors arranged along a line (using a two-dimensional detection) can be assayed each time, i.e. this not permitting simultaneous measurement of a two-dimensional sensor array by this angle detection method. After having installed the prepared gold film in systems of this kind, obtaining thermal equilibrium takes, however, some minutes (at least 15 minutes), i.e. the actual measurement then lasting at least until equilibrium of the molecular association is attained which may also take up some minutes. This is why systems of this kind lack good suitability in detecting the binding of a large number of different ligands, since the time and expense involved in measuring and changing the samples is relatively high.

A parallel approach to analyzing a sample array is SPR microscopy (SPM) (see: EP 388 874 A2 or M. Zizisperger, W. Knoll, Prog Colloid Polym Sci. 1998, 109 pages 244–253) in which the gold surface applied to a prism is coated in various portions with various samples and the gold surface imaged on a CCD chip at the SPR angle. During measurement the angle is varied by a mechanical scanner. However, this method is restricted to small object diameters.

A more recent SPR method is disclosed in WO 94/16312A1 in which detecting the binding of small amounts of substance is achieved by optical fiber guides partially coated with a gold film. However, here too, the problem still exists in designing a system required to assay a plurality of samples in parallel in accordance with this principle. Such an array of gold-coated fibers is, on the one hand, expensive and highly sensitive to mechanical stress, and, on the other, producing the array in parallel as proposed therein is difficult to achieve technically.

Optical fiber guides are also employed as it reads from WO 98/32002 A1. To protect them from being damaged physically the fiber cable is housed in a pipette. To achieve an array it is proposed to use a series arrangement of such pipettes. However, miniaturizing such an arrangement is difficult to achieve, especially for parallel measurement of many different samples.

Known from DE 196 15 366 A1 is a method and a means for the simultaneous detection of physical, biological or biochemical reactions and interactions at or in the surface of samples. All samples are simultaneously illuminated with monochromatic light and the reflected light supplied to a detection array, e.g. of a CCD matrix or video camera. The samples may be matrixed with the sensor surface areas in a single plane on a substrate plate located in turn on a transparent base plate which is illuminated. The electrical signals of the detection array are supplied to an analyzer. After analyzing the samples at one wavelength, the wavelength can be set to another value.

Known from WO 95/22754 is an analyzer in which a plurality of SPR analysis wells are arranged in a matrix for simultaneous assaying. The sensor surface areas of the analysis wells are located parallel in a single plane.

The invention is based on the object of defining a measurement assembly for simultaneous readout of a plurality of SPR sensors, more particularly exceeding a hundred or a thousand, in which readout is completed with a measuring time of less than thirty minutes.

This object is achieved by the measurement assembly and the measurement method as set forth in the independent claims, advantage aspects reading from the sub-claims.

To achieve this object, use is made of a specially configured array in an assembly with imaging methods to permit simultaneous readout. The array used for this purpose comprises a plurality of waveguides, it being noted that waveguide in this context is understood within the scope of the present invention to be an optical medium in which the light is guided in at least one dimension and which has at least two parallel interfaces.

The invention will now be detailed by way of examples illustrated diagrammatically in the drawings in which.

Figure 1:
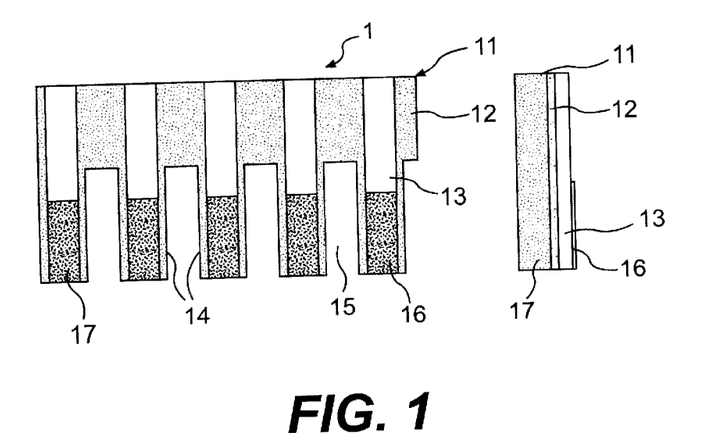
FIG. 1 is an illustration of one variant of part of a waveguide array employed.

Referring now to FIG. 1 there is illustrated how use is made to advantage within the scope of the present invention of a planar SPR sensor 1 suitable for being fabricated by known silicon semiconductor technologies and arranged into a waveguide array. Part of one such waveguide array is shown in FIG. 1. A wafer of silicon 11 is provided with a layer of $SiO_2$ 12 serving as an optical buffer relative to the waveguiding layer 13 and the silicon base material 11. The waveguide consists of a layer of silicon oxynitride 13 in a thickness down to approx. 10 µm. The silicon oxynitride layer 13 is patterned by a dry etching process so that parallel strips 14 materialize having widths in the range 10 µm to 2000 µm on a center-spacing in the range 10 µm to 5000 µm. Once the waveguide strips 14 have been patterned, the complete wafer is protected by a cover (not shown) except for the areas intended to form the substrate for the SPR-compatible metal layer 16 in a later process.

Subsequently, the exposed locations of the waveguide left unprotected in the previous step in the process are metallized in a thickness compatible with the requirements of the SPR measurement. The remaining cover of the wafer is removed. Depending on the technology employed for producing the comb-like recesses 15 in the substrate, these recesses may be produced before or after cited metallization.

The technology as described permits accommodating a plurality of parallel arrangements of waveguide patternings on a wafer which are then singled by means of etching silicon or sawing the silicon wafer. Separating each waveguide from the other, at the end locating the SPR sensor, is achievable by wet chemical etching the silicon or by a sawing process. Another variant in producing the waveguides consists of the possibility of producing polymers in thin films e.g. by centrifuging them onto a substrate. The polymers (e.g. PMMA, polycarbonate, UV-curing adhesives or siliconated polymers (cyclotenes or ORMOCERES)) present in dissolved or non-cured form are centrifuged or poured onto the substrate material. The refractive index of the substrate material must be smaller than that of the polymers to be applied, later representing the waveguide. When using UV-curing polymers, after homogenous application of the layer, the non-exposed portions are etched away so that narrow parallel strips of polymer remain on the substrate. Other polymers may be produced as strips by embossing or other replication techniques, the material remaining at the locations at which no light is to be guided needing to be dimensioned correspondingly thin. After the waveguide strips have been patterned, here too the complete wafer is protected by a cover except for the areas intended to carry the SPR-compatible metallization 16. In the next step these exposed areas are coated with the SPR-compatible metallization 16, after which the protective layer covering the remaining areas is removed.

The variants described permit production of a great many waveguides in parallel on a wafer. After fabrication of the waveguides with the SPR sensor surface areas, single strips consisting of a plurality of parallel waveguides are prepared from the processed wafer by a separating method, e.g. sawing. This singling process results in new face areas 17 which are prepared so that light can be coupled thereinto and thereout of.

The variants as described permit planar fabrication of a great many SPR sensors arranged in a row. To achieve an array of sensors several of these strips are arranged stacked horizontally. After assembly, such an array can be casted in a portion outside of the SPR-compatible metallization in a polymer to provide the SPR waveguide array with additional support. The arrangement and spacing of the individual SPR-compatible sensors may be made in accordance with the arrangement and spacing of the wells of a microtiter plate 60 (see FIG. 3) to be presented. When this is the case, the SPR waveguide array is brought into contact with the microtiter plate 60 carrying the samples 61 to be characterized, for measuring or coating the SPR-compatible layers 16 by introducing the SPR waveguide array into the microtiter plate 60 sufficiently until the SPR-compatible metallization is totally wetted by the samples 61. The individual vertical arranged waveguides can be arranged horizontally on the center-spacing of an optional microtiter format.

A waveguide array of the aforementioned kind is made use of in a first variant as will now be described with reference to FIG. 3.

Figures 3A, 3B:
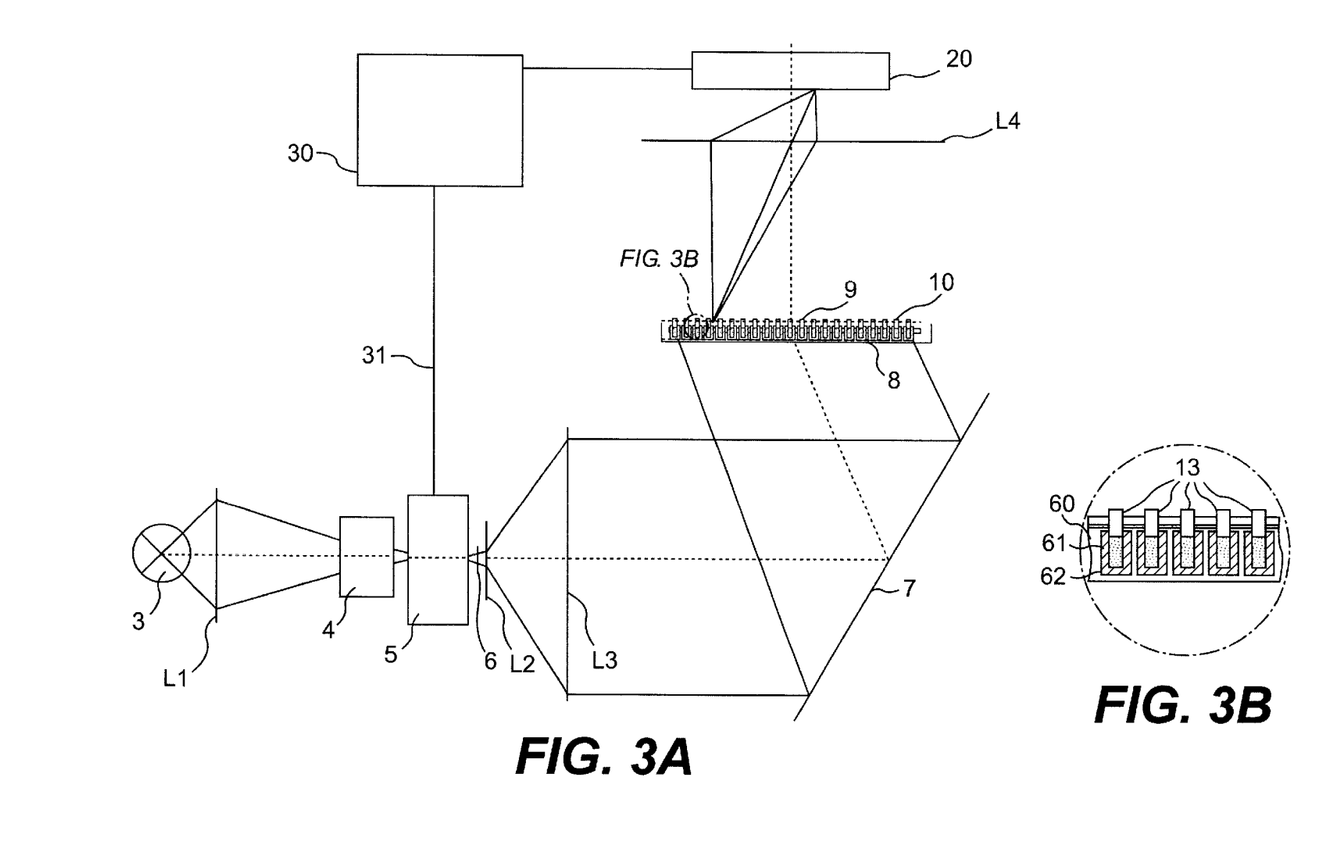
FIG. 3 is an illustration of a first variant of a measurement assembly in accordance with the present invention
Figures 6A, 6B:
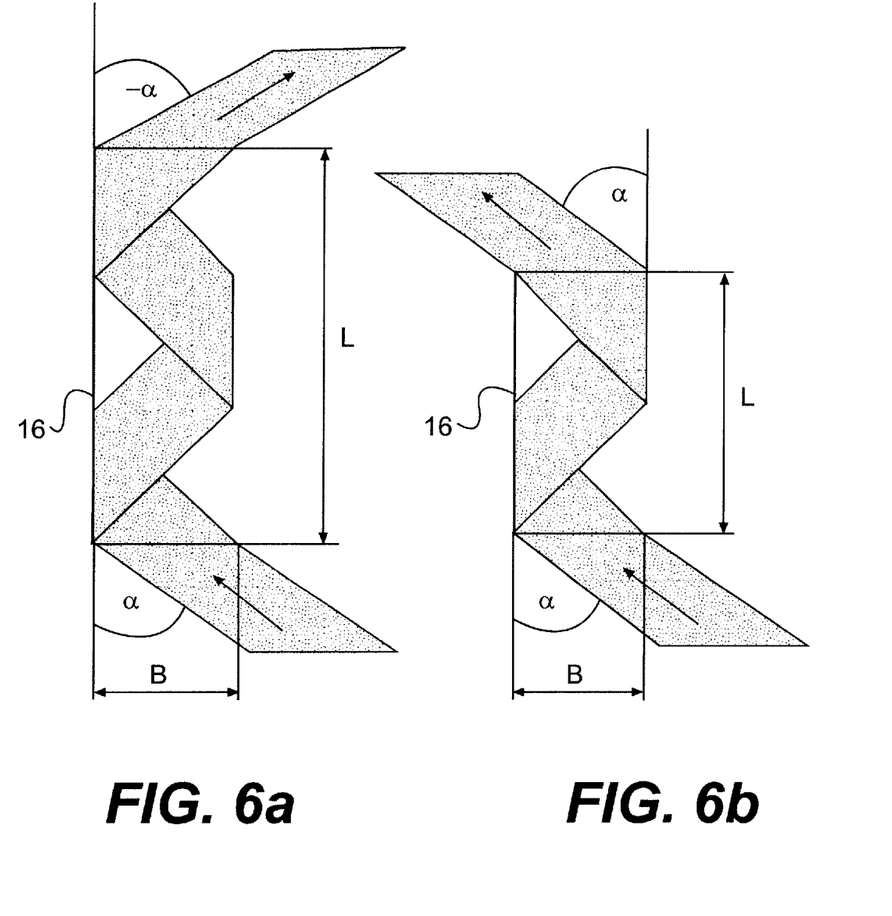
FIGS. 6a and 6b are illustrations of two different optical beam paths through the SPR-compatible surface area.

Referring now to FIG. 3 there is illustrated how only light in a bandwidth of approx. 0.5 to 5 nm is transmitted from the white light of a halogen lamp 3 after having passed through a suitable beam adapter optical system L1, an IR filter 4 inserted in the example to protect the optical components and a monochromator 5. As an alternative, selecting the wavelength may also be implemented with a filter wheel, requiring a corresponding number of filters having a similar bandwidth. Thereafter, in the example, the polarization direction is selected by a polarisator 6 for TM waves in respect of the SPR-compatible metallization 16 of the employed optical waveguide 13. An optical beam spreader L2, L3 then ensures parallel illumination of the complete waveguide array, in this example, via a folding mirror 7 applied so that the light is incident in the waveguide 13 at an angle of 70° to 90° relative to the normal of the gold film of the waveguides, since it is only light in this angle range that is capable of exciting plasmon resonance. Using a folding mirror in this case merely serves to make for a more compact configuration of the measurement assembly. As an alternative, illumination could also be made directly at this angle. A perforated mask 8 provided in the example as shown in FIG. 3 which may take one of many configurations, shades the portions behind which no waveguide is located to prevent scattered light from gaining access by some unwanted way to a detector furthermore provided. When some other technologically more complicated means of applying and locating a plurality of waveguides arranged in parallel is provided, as commercially available with a core diameter of approx. 200 µm, for example by embedding the individual waveguide sections in a common substrate, likewise in the scope of the present invention, then use may be made of a non-transparent material or a material having a non-transparent coating for the substrate material employed, as a result of which the perforated mask 8 as mentioned above can be eliminated. The waveguides themselves are located by their sensitive portion in a liquid which can be changed for implementing reference measurements in the various solutions to swap the target molecules or to implement washing. At the end of the waveguide remote from the sensitive waveguide portion the light emerges at an angle the same in amount as that with which it was incident into the other side (see FIG. 6). In the scope of the invention a dispersing means 9 is furthermore assigned to the waveguide sections at the light exit end, causing dispersion of the light emerging from the waveguides. This is achievable, for example, by means of a dispersing lamella to be applied separately, a suitable coating, or the like. This strongly divergent light is imaged directly by the objective lens L4 on a CCD chip 20, the objective lens L4 being designed to "see" the entirety of the waveguide array, but only a small proportion of the light emitted from an optical waveguide permitting detection. For detecting such small amounts of light, use is made in the example of a cooled high-sensitivity CCD chip 20, the necessary exposure time of which may amount to a few seconds.

Figure 2:
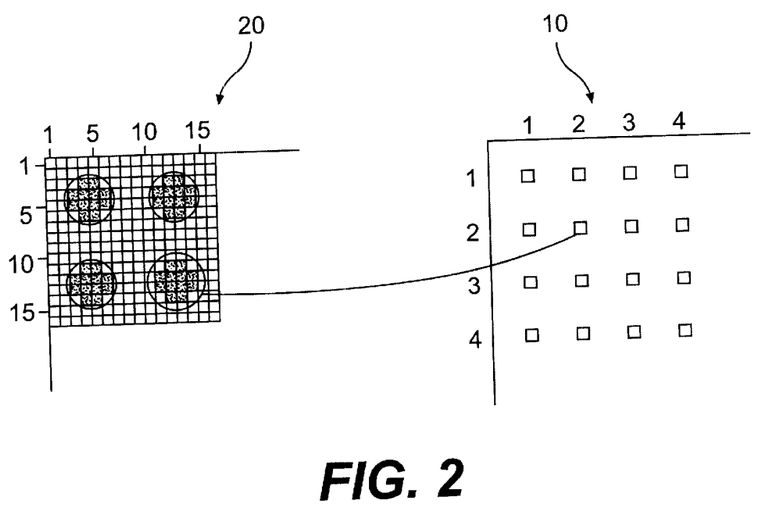
FIG. 2 is an illustration of how a single SPR-compatible sensor element is assigned to the pixels of a CCD array

It is provided for in the scope of the present invention that the light emerging from each waveguide is imaged on several CCD pixels simultaneously to enhance accuracy of detection. Thus, in the example, imaging is provided for on several camera pixels since a CCD chip has a great many more pixels than the waveguide array provided for in this case at the individual waveguides. Within the scope of the present invention, an image processing software is employed for assigning the portion of several CCD pixels to each waveguide. This is indicated diagrammatically in FIG. 2, e.g. waveguide 2,2 being assigned the pixel portion {(11,12), (11,13), . . . ,(14,13)}, i.e. the portion of the CCD chip 20 for imaging the waveguide 2,2 comprises 12 pixels. This assignment is memorized in a computer 30 and remains available for the complete duration of the subsequent measurement, since the array is no longer moved further. A fast program algorithm obtains the sum of these camera pixel portions assigned to each waveguide so that a discrete intensity value is obtained and memorized for each waveguide. The wavelength of the light incident from underneath in the example, is then shifted by approx. 1 nm with the aid of the monochromator 5 signalled by the computer 30 to obtain the next intensity value for all waveguides to thus obtain an intensity spectrum specific to each and every waveguide. To optimize the measuring time needed for imaging such a spectrum, the exposure of the CCD camera is instantly restarted, once the data relative to the last wavelength have gained access to the computer memory and a new wavelength is set at a monochromator 5 signalled by a stepper motor. Summing the results in the computer as to the pixel maps can then be undertaken during the time needed for exposing the new wavelength, When this time is sufficiently long, the time needed for computing the summation is negligible. The time needed for each wavelength is dictated substantially by the exposure time, which in the example is approx. 5 seconds, 16 minutes thus being needed for a spectrum of 200 nm. Now, to determine the molecules associating with each SPR sensor of every individual waveguide, it is not the absolute intensity spectrum of a single measurement, but the difference in the minima of the intensity spectra for a measurement in a pure buffer solution as compared to those of a second measurement in the presence of the target molecule, i.e. it is this shift in the wavelength that first permits arriving at an indication as to the molecular association. Accordingly, sequencing reference and sample measurements would be possible within 32 minutes for all waveguide sensors illuminated.

Figure 4:
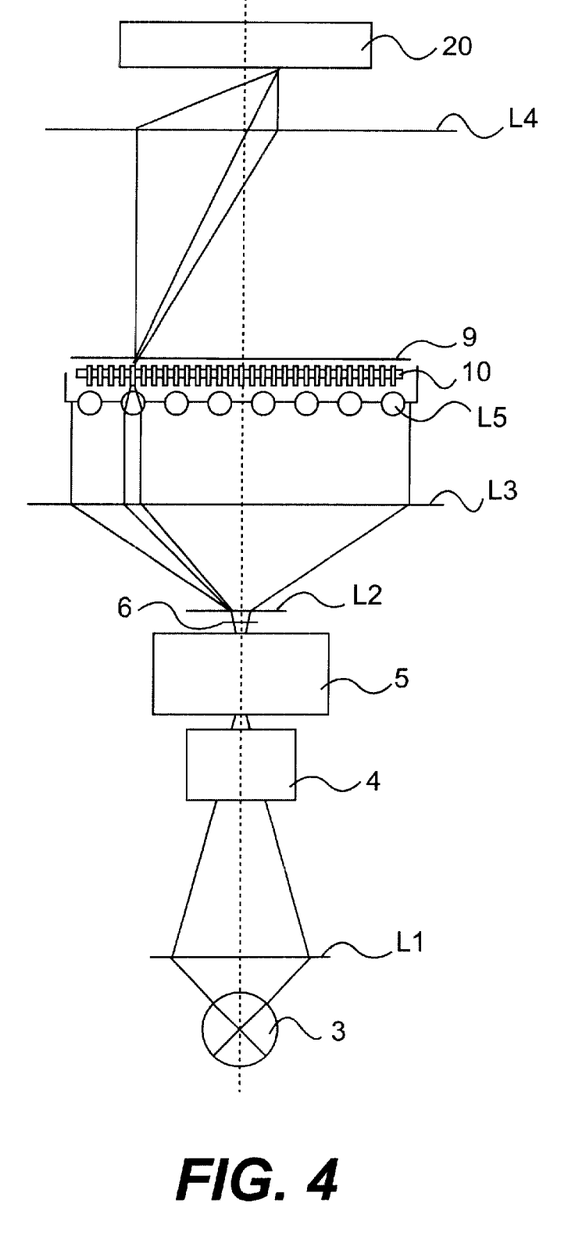
FIG. 4 is an illustration of a second variant of a measurement assembly in accordance with the present invention

Referring now to FIG. 4 there is illustrated diagrammatically another variant of the assembly in accordance with the invention which reduces the time needed for the measurement. Since it is the time needed for the exposure which is the time-limiting factor, the measurement time can be shortened by increasing the amount of light in the waveguides. For this purpose a more powerful light source 3, such as e.g. a Xenon arc lamp may be employed, The same as in the arrangement as shown in FIG. 3, the light first passes through an IR filter 4, a monochromator 5 and a polarisator 6, an optical beam spreader L2, L3 then assuring parallel illumination of the waveguide array 10, upstream of which in this embodiment spherical or gradient lenses L5 are inserted. To illuminate all waveguides in the example as shown in FIG. 4, however, several new positionings of the waveguide array 10, relative to the lenses L5 provided, are needed. However, assigning a separate lens to each waveguide is likewise within the scope of the present invention whereby this lens may also be a component in the wells 62 of the microtiter plate concerned.

The parallel light is focussed by the lenses L5 into the waveguides, coated with gold, for example, such that in the sensitive portion of the waveguide the diverging rays are incident at the provided metallization of the waveguide also at the angle permitting SPR detection. As compared to the exposure arrangement as shown in FIG. 3 the lenses L5 as provided in the example permit inputting roughly 100 times the light intensity into the waveguides. The entrance windows 17 of the waveguides in this example are positioned at the focal point of the lenses, i.e. at a distance of a few 100 μm. In this arrangement it is to be assured that no light bypasses the waveguide, for instance due to any interspaces or transparencies, into the space for light exit from the waveguides. Here too, this can be avoided by providing the means as described above, for example a perforated mask 8. At the light exit end of the waveguides the light emerges from the optical waveguide again divergent and is likewise imaged on a CCD chip 20 with the aid of a dispersing means 9 and an objective lens L4.

Figure 10A:
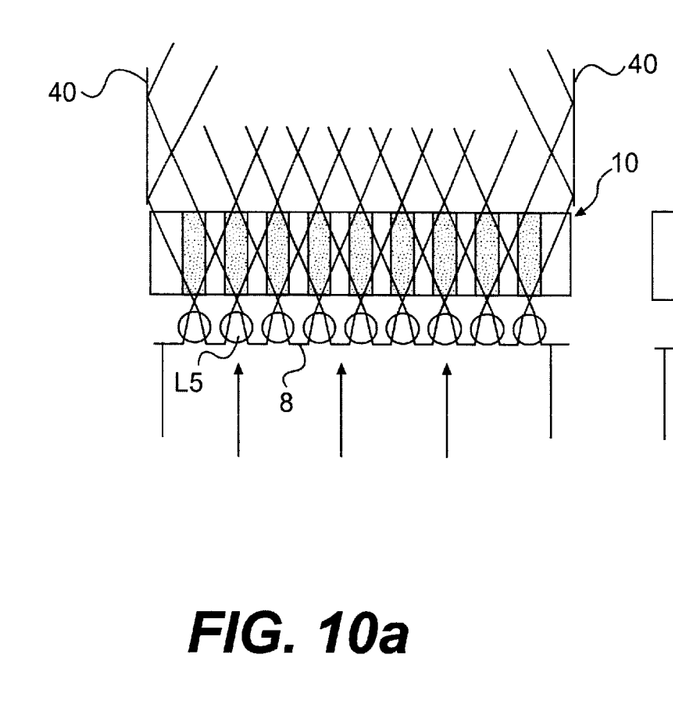
Figure 10B:
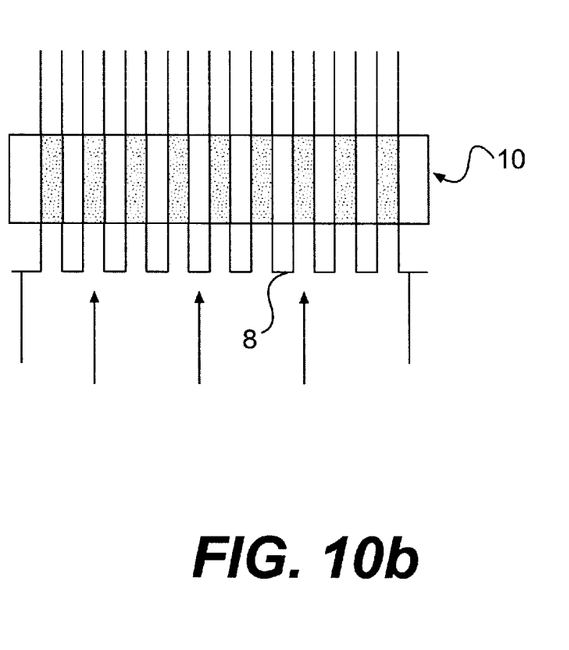

The further assignment and analysis of the light intensities assigned to each optical waveguide is the same as described with reference to FIG. 3. For each wavelength, the time needed can now be reduced to approx. 1 second due to the higher light intensity. When restricting the arrangement to e.g. a spectrum of sixty wavelengths, the time needed for measuring all spectra in parallel in the example is one minute, thus making it possible to implement e.g. kinetic binding assays simultaneously with a large number of ligands. Referring now to FIGS. 10*a* and 10*b* the difference between illuminating the waveguide array 10 with divergent light in accordance with the embodiment as shown in FIG. 4 and with parallel light as shown in FIG. 3 will now be demonstrated. These Figs. illustrate the marginal rays after having passed through the perforated mask 8 against the background of a line of sensors. In the divergent case (FIG. 10*a*) the marginal rays sweep several measuring ranges so that after emergence the marginal ray can no longer be assigned to a single measuring range, this being the reason why when illuminating with divergent light, interfaces 40 are to be included at the margin of the sensor area to ensure total reflection, whereas when illuminating with parallel light (FIG. 10*b*) these margin areas can be eliminated. In this arrangement the light beam is guided solely by total reflection at the sensor area and the opposite surface. In this case the light beam penetrates the waveguides at a angle suitable for SPR resonance right from the start. When then being successful in imaging the entirety of the parallel emergent light on a CCD detection, it is likewise possible to increase the intensity and thus to shorten the time needed for measurement, except that in this case unlike the situation as shown in FIG. 3, the angle of the incident light is fixedly defined.

Figure 5:
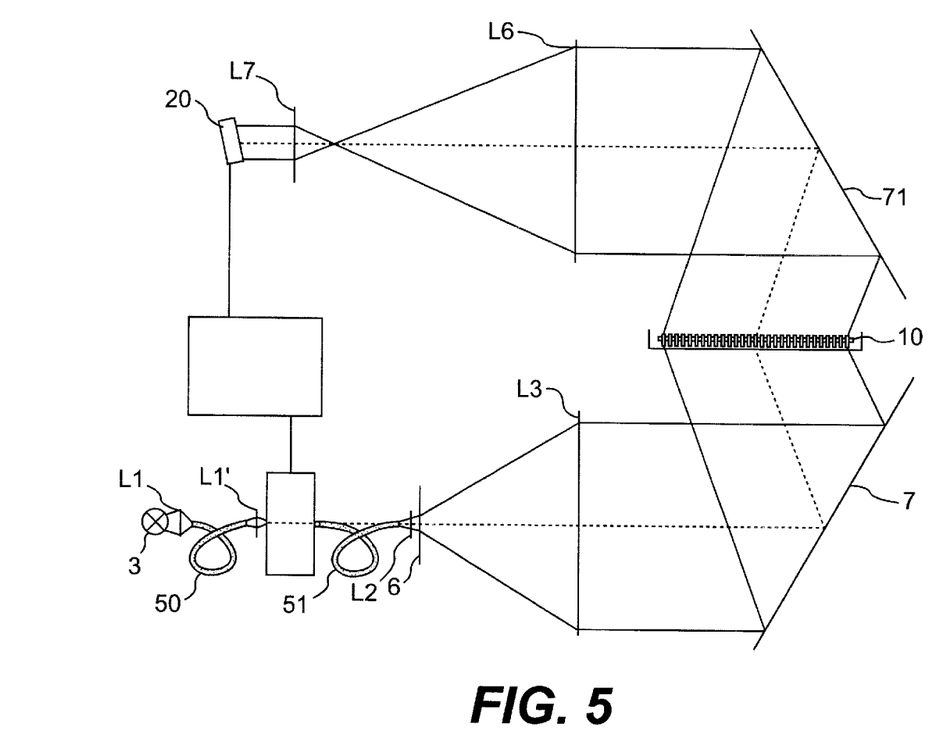
FIG. 5 is an illustration of a third variant of a measurement assembly in accordance with the present invention

Referring now to FIG. 5 there is illustrated a more complicated embodiment, working on the principle of total parallel ray path and achieving additionally improved imaging performance (less edge shading, lower sensitivity to scattered light). In this case the light is guided through an optical fiber 50 via an optical imaging system L1,L1' to the monochromator 5 and through a further optical fiber 51 to an optical beam spreader L2, L3. This has the advantage that guiding the illuminating beam can be adjusted independently of the light being coupled into and out of the monochromator 5. Illuminating the waveguide array 10 is done the same as described in FIG. 3 with a spread parallel bundled rays at the plasmon resonance angle, a perforated mask (not shown in FIG. 5) being employed optionally as shown in FIG. 3. In emerging from the sensor the light is either parallel displaced (for an even number of reflections, cf. FIG. 6b) and thus at the angle a the same as on entry, or for an uneven number of reflections (FIG. 6a) it emerges at an angle $-\alpha$. The length L and width B of the SPR-compatible waveguide are specially dimensioned in the example as shown in FIG. 5 so that the number of reflections is uneven and thus the light emerges exclusively in the direction of a second folding mirror 71. Unlike the situation as shown in FIG. 3 in which imaging on a CCD camera is achieved with a scattering layer, in this case the parallelism of the emerging light is made use of to practically reverse the illuminating light path. Via an achromatic collimator lens L6 of long focal length (e.g. f=1000 mm) and large diameter and a suitable objective lens L7 (e.g. f=100 mm) the surface area of the sensor array is imaged on the CCD chip like in a telescope. Since the surface of the waveguide array 10 to be imaged does not stand perpendicular to the optical axis of the arrangement, using a conventional camera, i.e. with the objective lens parallel to the CCD chip would result in only a line of the object being sharply focussed because of the inadequate depth of focus. This is why on the imaging side the CCD chip 20 needs to be likewise tilted relative to the optical axis, as indicated in FIG. 5, to ensure a sharp image of the whole sensor array surface area 10. This is achievable by tilting the CCD camera with a goniometer (not shown) relative to the objective lens. Another advantage of telescopic imaging is its low sensitivity to scattered light, since it is only the light emerging at the detection angle from the plane of the object that is imaged on the CCD chip.

Figure 7:
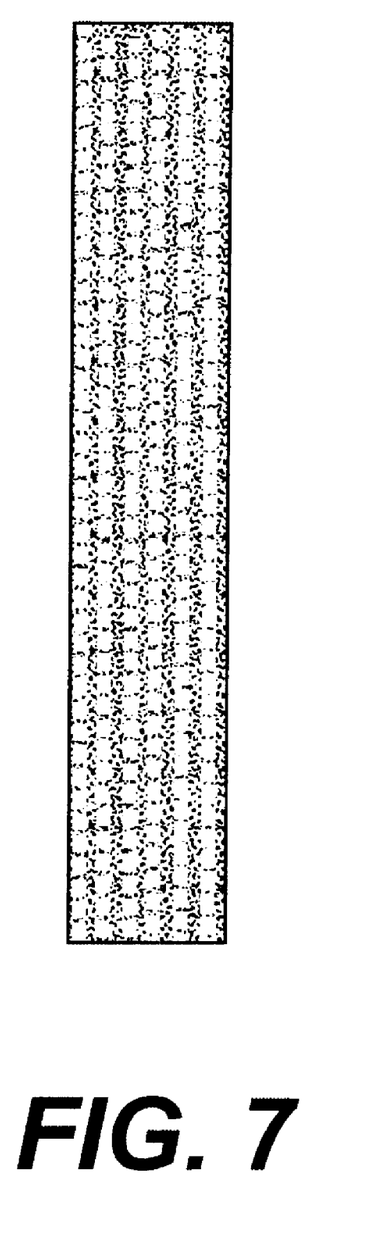
FIG. 7 is a CCD image of a SPR waveguide array.
Figure 8:
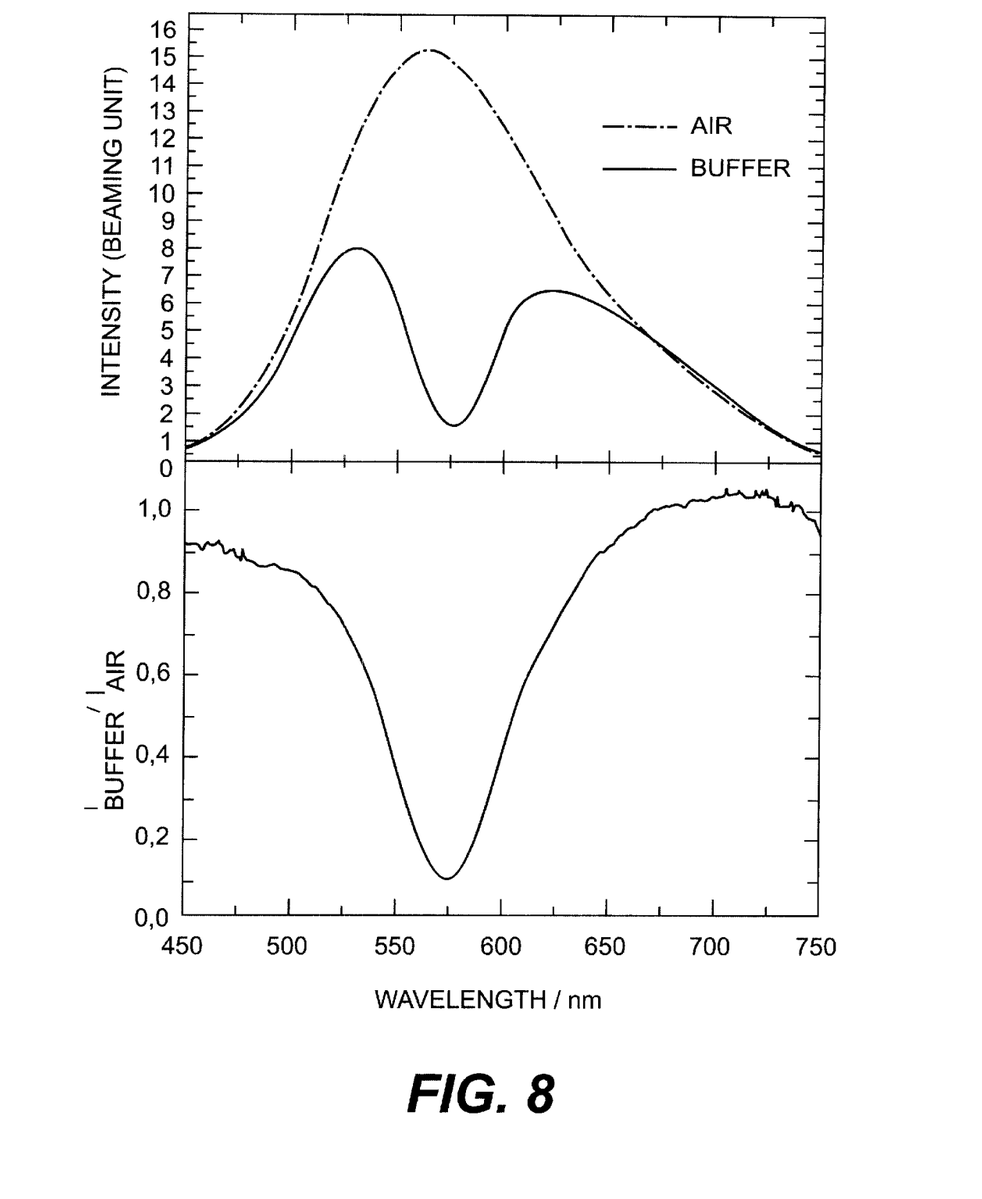
FIG. 8 is a plot of the intensity profile of a single SPR-compatible waveguide.

Referring now to FIG. 7 there is illustrated a sharp image of a sensor array 10 as produced by the optical arrangement as shown in FIG. 5. Such an image is detected for each wavelength and in the computer 30 the intensity integral as a function of a sensor surface area is formed, as described above with reference to FIG. 2. It is in this way that for each and every sensor a drop in the intensity as materializing in surface plasmon resonance, is detected in the spectrum as shown in FIG. 8 by way of example for a single case. The broken line curve in the upper portion of FIG. 8 shows the spectrum with the sensor surface area located in air, this substantially corresponding to mathematically folding the lamp spectrum and monochromatic transmission. The solid line corresponds to the measurement in the presence of a buffer; this spectrum is superimposed by the surface plasmon resonance. As shown in the lower portion of FIG. 8 obtaining the pure surface plasmon resonance spectrum is done by scaling to the spectrum in air.

Figure 9A:
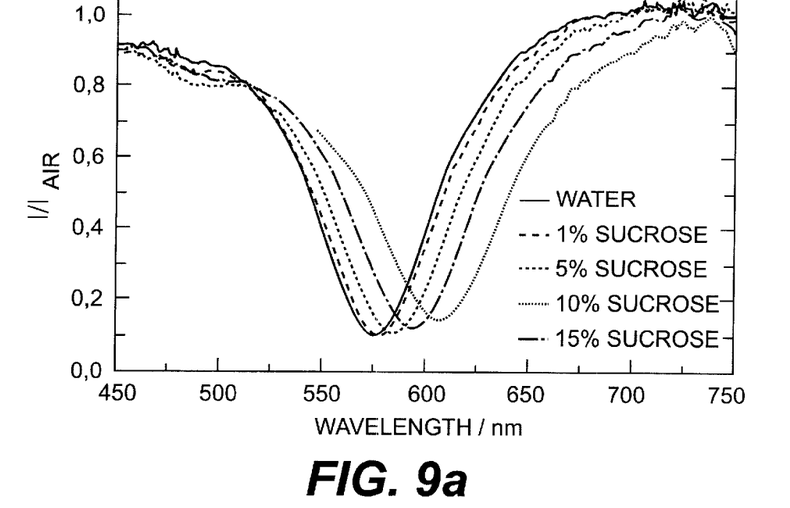
FIG. 9 is a plot of how the intensity profile is shifted for differences in the sample concentration and FIGS. 10a and 10b illustrate the difference between illuminating the waveguide array 10 with divergent light in accordance with one embodiment as shown in FIG. 4 and with parallel light as shown in FIGS. 3 and 5.
Figure 9B:
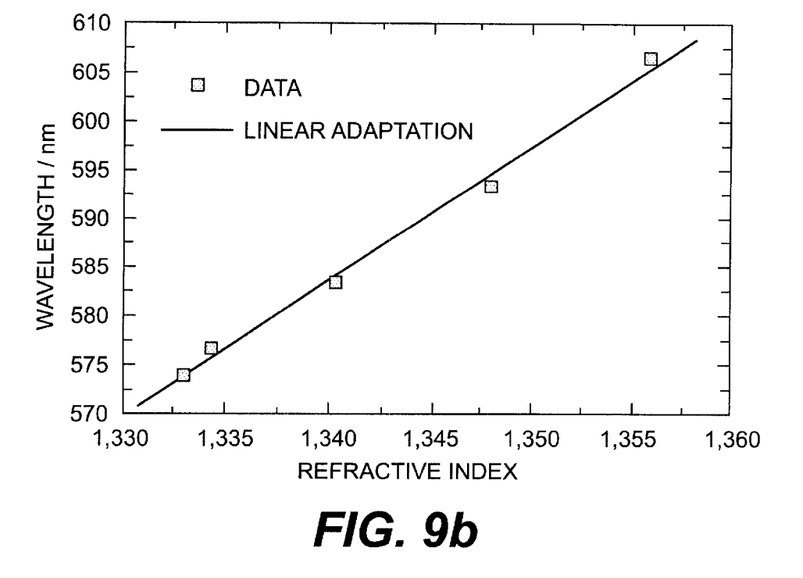

To verify that the detected drop in the spectrum is surface plasmon resonance, the refractive index of the solution is varied by making the measurement in various sucrose concentrations. It is evident from the upper portion of FIG. 9 how the drop in the spectrum is shifted, as expected, with increasing sucrose concentration. Adapting the measurement data with a Gauss function furnishes numerical values for the location of the minima of the spectra, from which, with the known refractive index of the solution, a calibration curve is obtained as shown in the lower portion of FIG. 9. For a sufficiently small range of the refractive index an approximately linear relationship is assumed. In the present example a shift of 1.4 nm is obtained for a change in the refractive index of $10^{-3}$ in enabling the minimum to be determined with an accuracy of approx. 0.3 nm, a typical value for a resonance curve of approx. 50 nm half-value width. Thus changes in the refractive index of $2 \cdot 10^{-4}$ can be detected. This demonstrates the sensitivity of the method for parallel measurement of several hundred or thousand samples within a few minutes.

List of Reference Numerals

1—planar SPR sensor
10—waveguide array
11—wafer of silicon
12—$SiO_2$ layer
13—optical waveguide
14—waveguide strips
15—comb-like recesses
16—SPR-compatible layer
17—face areas (entrance windows) of 13
20—CCD chip (camera) 20
3—light source
4—IR filter
5—wavelength-selective assembly
6—polarisator
7—folding mirror
71—second folding mirror
8—perforated mask
9—light dispersing means
30—computer
31—control line
40—reflective interfaces
50,51—optical fiber
60—microtiter plate
61—sample in a well of a microtiter plate
62—wells
B—width of SPR-compatible waveguide
L—length of SPR-compatible waveguide
α—angle of light entry/exit
L1,L1',L2,L3,L4,L6,L7—optical imaging systems
L5—lenses

What is claimed is:

1. A surface plasmon resonance (SPR) measurement assembly, comprising:
   a waveguide array comprising a plurality of planar waveguides into which light is guided via a light entrance side and a light exit side in at least one dimension, and each of which comprises at least two parallel interfaces, the center-spacing of said individual waveguides corresponding to a one or two-dimensional regular matrix and each and every waveguide is provided with a SPR-compatible sensor area;

a light source;

a wavelength-selective assembly and an optical system downstream of said light source, said optical system being configured so that said light entrance sides of said waveguides of said waveguide array are illuminated in parallel, said wavelength-selective assembly being configured to set the wavelength of said light to a predefined light wavelength;

an imaging optical system and a CCD chip configured so that said light emerging from each and every waveguide is detected by a cluster of CCD pixels of said CCD chip in each case; and a computer including image processing software configured so that a light intensity value of said light emerging from each and every waveguides is computed and following data storage of said intensity value, set wavelength and coordinates of said waveguide array said wavelength-selective assembly is set to a further light wavelength via a control line for the purpose of imaging an intensity spectrum.

2. The measurement assembly as set forth in claim 1, characterized in that a polarisator is arranged downstream of said wavelength-selective assembly.

3. The measurement assembly as set forth in claim 1, characterized in that said waveguides are configured comb-shaped and their matrix adapted to the well arrangement of a microtliter plate, at least a bottom portion of said wells being configured optically transparent so that light from said waveguide array incident in said wells is detected.

4. The measurement assembly as set forth in claim 3, characterized in that said masking and/or absorption means are assigned to ensure that the light enters only the bottom portion of said wells of said microtiter plate in which SPR-compatible sensors are arranged.

5. The measurement assembly as set forth in claim 3, characterized in that said absorption means assigned to said light entrance side of said waveguide array take the form of a microtiter plate whose well sidewalls are fabricated of a light-absorbing material.

6. The measurement assembly as set forth in claim 1, characterized in that dispersing means are assigned to the light exit side of said waveguide array.

7. The measurement assembly as set forth in claim 1, characterized in that masking and/or absorption means are assigned to the light entrance side of said waveguide array to ensure that only the light emerging from said waveguides gains access to said CCD chip.

8. The measurement assembly as set forth in claim 7, characterized in that masking means in the form of a perforated mask are assigned to said light entrance side of said waveguide array.

9. The measurement assembly as set forth in claim 7, characterized in that said absorption means assigned to said light entrance side of said waveguide array take the form of a light-absorbing cast separating said waveguides from each other.

10. The measurement assembly as set forth in claim 1, characterized in that said wavelength-selective assembly is formed by an incrementally variable monochromator and said optical imaging system is followed by a folding mirror ensuring parallel illumination of said light entrance side of said waveguides at a suitable angle.

11. The measurement assembly as set forth in claim 10, characterized in that said light exit side end of said waveguide array is additionally provided directly downstream with a further folding mirror ensuring imaging of said waveguide array on a CCD chip inclined to the optical axis.

12. The measurement assembly as set forth in claim 1, characterized in that said wavelength-selective assembly is formed by an incrementally variable monochromator and said optical imaging system assures parallel perpendicular illumination of said light entrance side of said waveguide array, each optical waveguide being provided upstream with a lens ensuring divergent illumination of said SPR-compatible metallizations of said waveguides.

13. A surface plasmon resonance (SPR) measurement method comprising the following steps:

using a waveguide array comprising a plurality of waveguides into which light is guided via a light entrance side and a light exit side in at least one dimension and each of which comprises at least two parallel interfaces, the center-spacing of said individual waveguides corresponding to a one or two-dimensional regular matrix and each and every waveguide is provided with a SPR-compatible sensor area;

illuminating in parallel said light entrance sides of said waveguides of said waveguide array by a light source, a wavelength-selective assembly and an optical system, said wavelength-selective assembly being configured to set the wavelength of the light to a predefined light wavelength;

imaging the light emerging from the light exit sides of said waveguides of said waveguide array on a CCD chip with an imaging optical system and detecting the light emerging from each and every optical waveguide by a cluster of CCD pixels of said CCD chip in each case; and computing a light intensity value of the light emerging from each and every optical waveguide by a computer including image processing software and following data storage of said intensity value, set wavelength and coordinates of said waveguide array, said wavelength-selective assembly being set to a further light wavelength for the purpose of imaging an intensity spectrum.

14. The measurement method as set forth in claim 13, characterized in that a polarisator is arranged downstream of said wavelength-selective assembly.

15. The measurement method as set forth in claim 13, characterized in that said waveguides are configured comb-shaped and their matrix adapted to the well arrangement of a microtiter plate, at least a bottom portion of said wells is configured optically transparent so that light from said waveguide array incident in said wells is detected.

16. The measurement method as set forth in claim 15, characterized in that said masking and/or absorption means are assigned to ensure that said light enters only the bottom portion of said wells of said microtiter plate in which SPR-compatible sensors are arranged.

17. The measurement method as set forth in claim 15, characterized in that said absorption means assigned to said light entrance side of said waveguide array take the form of a microtiter plate whose well sidewalls are fabricated of a light-absorbing material.

18. The measurement method as set forth in claim 13, characterized in that dispersing means are assigned to said light exit side of said waveguide array.

19. The measurement method as set forth in claim 13, characterized in that masking and/or absorption means are assigned to said light entrance side of said waveguide array to ensure that only the light emerging from said waveguides gains access to said CCD chip.

20. The measurement method as set forth in claim 19, characterized in that masking means in the form of a perforated mask are assigned to said light entrance side of said waveguide array.

21. The measurement method as set forth in claim 19, characterized in that said absorption means assigned to said light entrance side of said waveguide array take the form of a light-absorbing cast separating said waveguides from each other.

22. The measurement method as set forth in claim 21, characterized in that said light exit side end of said waveguide array is additionally provided directly downstream with a further folding mirror ensuring imaging of said waveguide array on a CCD chip inclined to the optical axis.

23. The measurement method as set forth in claim 13, characterized in that said wavelength-selective assembly is formed by an incrementally variable monochromator and said optical imaging system is followed by a folding mirror ensuring parallel illumination of said light entrance side of said waveguides at a suitable angle.

24. The measurement method as set forth in claim 13, characterized in that said wavelength-selective assembly is formed by an incrementally variable monochromator and said optical imaging system assures parallel perpendicular illumination of said light entrance side of said waveguide array, each waveguide being provided upstream with a lens ensuring divergent illumination of said SPR-compatible metallizations of said waveguides.

* * * * *

UNITED STATES PATENT AND TRADEMARK OFFICE
CERTIFICATE OF CORRECTION

PATENT NO.   : 6,441,906 B2
DATED        : August 27, 2002
INVENTOR(S)  : Stefan Dickopf et al.

It is certified that error appears in the above-identified patent and that said Letters Patent is hereby corrected as shown below:

<u>Column 9,</u>
Line 26, change "microtliter" to -- microtiter --.

Signed and Sealed this

Thirty-first Day of December, 2002

JAMES E. ROGAN
*Director of the United States Patent and Trademark Office*